US006265541B1

(12) United States Patent
Olivera et al.

(10) Patent No.: US 6,265,541 B1
(45) Date of Patent: Jul. 24, 2001

(54) USES OF α-CONOTOXIN PEPTIDES

(75) Inventors: Baldomero M. Olivera; J. Michael McIntosh; Doju Yoshikami; G. Edward Cartier; Siqin Luo, all of Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/219,446

(22) Filed: Dec. 23, 1998

Related U.S. Application Data

(60) Provisional application No. 60/070,153, filed on Dec. 31, 1997, and provisional application No. 60/080,588, filed on Apr. 3, 1998.

(51) Int. Cl.[7] .................. C07K 14/00; C07K 14/435; C12N 15/12; A61K 38/00
(52) U.S. Cl. .............. 530/326; 530/326; 530/300; 530/324; 514/12; 514/13; 514/2
(58) Field of Search .................. 530/326, 324, 530/300; 514/2, 12, 13

(56) References Cited

U.S. PATENT DOCUMENTS

| 4,447,356 | 5/1984 | Olivera et al. | 260/112.5 |
|---|---|---|---|
| 5,432,155 | 7/1995 | Olivera et al. | 514/12 |
| 5,514,774 | 5/1996 | Olivera et al. | 530/324 |
| 5,595,972 | 1/1997 | Olivera et al. | 514/13 |
| 5,633,347 | 5/1997 | Olivera et al. | 530/324 |
| 5,866,682 | 2/1999 | McIntosh et al. | 530/326 |

FOREIGN PATENT DOCUMENTS

| 9511256 | 4/1995 | (WO) . |
|---|---|---|
| 9822196 | 5/1998 | (WO) . |
| 9824462 | 6/1998 | (WO) . |

OTHER PUBLICATIONS

Kulak, J.M. et al. (1997). "α–Conotoxin MII Blocks Nicotine–Stimulated Dopamine Release in Rat Striatal Synaptosomes," *J. of Neurosci.* 17(14):5263–70.

Tavazoie, S.F. et al. (1997). "Differential block of nicotinic synapses on B versus C neurones in sympathetic ganglia of frog by α–conotoxins MII and ImI," *Brit. J. Pharmacol.* 120:995–1000.

Fainzilber, M. et al. (1994). "New Mollusc–Specific α–Conotoxins Block *Aplysia* Neuronal Acetylcholine Receptors," *Biochemistry* 33:9523–29.

*Primary Examiner*—Karen Cochrane Carlson
*Assistant Examiner*—Patricia Robinson
(74) *Attorney, Agent, or Firm*—Rothwell, Figg, Ernst & Manbeck, pc

(57) ABSTRACT

The present invention relates to the use of α-conotoxin peptides having the general formula $$Xaa_1\text{-}Xaa_2\text{-}Cys\text{-}Cys\text{-}Xaa_3\text{-}Xaa_4\text{-}Pro\text{-}Xaa_5\text{-}Cys\text{-}Xaa_6\text{-}Cys \text{ (SEQ ID NO: 1)}$$

for treating disorders regulated at neuronal nicotinic acetylcholine receptors. Such disorders include, but are not limited to, cardiovascular disorders, gastric motility disorders, urinary incontinence, nicotine addiction, mood disorders (such as bipolar disorder, unipolar depression, dysthymia and seasonal effective disorder) and small cell lung carcinoma, as well as the localization of small cell lung carcinoma. In this formula, $Xaa_1$ is des-$Xaa_1$, Tyr, mono-iodo-Tyr or di-iodo-Tyr, $Xaa_2$ is any amino acid, $Xaa_3$ is any amino acid, $Xaa_4$ is any amino acid, $Xaa_5$ is any amino acid and $Xaa_6$ represents a peptide of 3–7 amino acids. Disulfide linkages exist between the first and third cysteines and the second and fourth cysteines. Pro may be replaced with hydroxy-Pro. The C-terminus may contain a hydroxyl or an amide group, preferably an amide group.

19 Claims, 3 Drawing Sheets

SEQUENCE LISTING

```
<160> NUMBER OF SEQ ID NOS:  13

<210> SEQ ID NO 1
<211> LENGTH: 17
<212> TYPE: PRT
<213> ORGANISM: Artificial Sequence
```

```
<220> FEATURE:
<223> OTHER INFORMATION: Description of Artificial Sequence:generic
      alpha-conotoxin sequence
<221> NAME/KEY: PEPTIDE
<222> LOCATION: (1)..(6)
<223> OTHER INFORMATION: Xaa at residue 1 is des-Xaa, Tyr,
      mono-iodo-Tyr or di-iodo-Tyr; Xaa at residue 2 is any amino acid;
      Xaa at residue 5 is any amino acid; Xaa at residue
      6 is any amino acid.
<221> NAME/KEY: PEPTIDE
<222> LOCATION: (8)..(12)
<223> OTHER INFORMATION: Xaa at residues 8, 10, 11 and 12  may be any
      amino acid; Xaa at residues 13, 14, 15 and 16  may be
      des-Xaa or  any amino acid.

<400> SEQUENCE: 1

Xaa Xaa Cys Cys Xaa Xaa Pro Xaa Cys Xaa Xaa Xaa Xaa Xaa Xaa
 1               5                  10                  15

Cys

<210> SEQ ID NO 2
<211> LENGTH: 16
<212> TYPE: PRT
<213> ORGANISM: Conus magus

<400> SEQUENCE: 2

Gly Cys Cys Ser Asn Pro Val Cys His Leu Glu His Ser Asn Leu Cys
 1               5                  10                  15

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence:Tyr
      derivative of C. magus MII

<400> SEQUENCE: 3

Tyr Gly Cys Cys Ser Asn Pro Val Cys His Leu Glu His Ser Asn Leu
 1               5                  10                  15

Cys

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence:FAT
      derivative of C. magus MII

<400> SEQUENCE: 4

Gly Cys Cys Ser Asn Pro Val Cys Phe Ala Thr His Ser Asn Leu Cys
 1               5                  10                  15

<210> SEQ ID NO 5
<211> LENGTH: 16
<212> TYPE: PRT
<213> ORGANISM: Conus aulicus

<400> SEQUENCE: 5

Gly Cys Cys Ser Tyr Pro Pro Cys Phe Ala Thr Asn Ser Asp Tyr Cys
 1               5                  10                  15

<210> SEQ ID NO 6
<211> LENGTH: 17
<212> TYPE: PRT
<213> ORGANISM: Artificial Sequence
```

<220> FEATURE:
<223> OTHER INFORMATION: Description of Artificial Sequence:Tyr
      derivative of C. aulicus AuIA

<400> SEQUENCE: 6

Tyr Gly Cys Cys Ser Tyr Pro Pro Cys Phe Ala Thr Asn Ser Asp Tyr
 1               5                  10                  15

Cys

<210> SEQ ID NO 7
<211> LENGTH: 15
<212> TYPE: PRT
<213> ORGANISM: Conus aulicus

<400> SEQUENCE: 7

Gly Cys Cys Ser Tyr Pro Pro Cys Phe Ala Thr Asn Ser Asp Cys
 1               5                  10                  15

<210> SEQ ID NO 8
<211> LENGTH: 16
<212> TYPE: PRT
<213> ORGANISM: Conus aulicus

<400> SEQUENCE: 8

Gly Cys Cys Ser Tyr Pro Pro Cys Phe Ala Thr Asn Ser Gly Tyr Cys
 1               5                  10                  15

<210> SEQ ID NO 9
<211> LENGTH: 16
<212> TYPE: PRT
<213> ORGANISM: Conus purpurascens

<400> SEQUENCE: 9

Gly Cys Cys Ser Leu Pro Pro Cys Ala Ala Asn Asn Pro Asp Tyr Cys
 1               5                  10                  15

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence:A10L
      derivative of C. purpurascens PnIA

<400> SEQUENCE: 10

Gly Cys Cys Ser Leu Pro Pro Cys Ala Leu Asn Asn Pro Asp Tyr Cys
 1               5                  10                  15

<210> SEQ ID NO 11
<211> LENGTH: 16
<212> TYPE: PRT
<213> ORGANISM: Artificial Sequence
<220> FEATURE:
<223> OTHER INFORMATION: Description of Artificial Sequence:N11S
      derivative of C. purpurascens PnIA

<400> SEQUENCE: 11

Gly Cys Cys Ser Leu Pro Pro Cys Ala Ala Ser Asn Pro Asp Tyr Cys
 1               5                  10                  15

<210> SEQ ID NO 12
<211> LENGTH: 16
<212> TYPE: PRT
<213> ORGANISM: Conus purpurascens

<400> SEQUENCE: 12

-continued

```
Gly Cys Cys Ser Leu Pro Pro Cys Ala Leu Ser Asn Pro Asp Tyr Cys
  1               5                  10                  15

<210> SEQ ID NO 13
<211> LENGTH: 12
<212> TYPE: PRT
<213> ORGANISM: Conus imperialis

<400> SEQUENCE: 13

Gly Cys Cys Ser Asp Pro Arg Cys Ala Trp Arg Cys
  1               5                  10
```

USES OF α-CONOTOXIN PEPTIDES

CROSS-REFERENCE TO RELATED APPLICATIONS

The present application is related to U.S. provisional patent application No. 60/070,153, filed Dec. 31, 1997 and to U.S. provisional patent application No. 60/080,588, filed Apr. 3, 1998, each incorporated herein by reference.

This invention was made with Government support under Grant Nos. GM48677 and MH53631 awarded by the National Institutes of Health, Bethesda, Md. The United States Government has certain rights in the invention.

BACKGROUND OF THE INVENTION

This invention relates to uses of relatively short peptides about 14–17 residues in length, which are naturally available in minute amounts in the venom of the cone snails or analogs to the naturally available peptides, and which include two cyclizing disulfide linkages.

The publications and other materials used herein to illuminate the background of the invention, and in particular, cases to provide additional details respecting the practice, are incorporated by reference, and for convenience are referenced in the following text by author and date and are listed alphabetically by author in the appended bibliography.

Mollusks of the genus Conus produce a venom that enables them to carry out their unique predatory lifestyle. Prey are immobilized by the venom that is injected by means of a highly specialized venom apparatus, a disposable hollow tooth that functions both in the manner of a harpoon and a hypodermic needle.

Few interactions between organisms are more striking than those between a venomous animal and its envenomated victim. Venom may be used as a primary weapon to capture prey or as a defense mechanism. Many of these venoms contain molecules directed to receptors and ion channels of neuromuscullar systems.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used, however, every Cones species uses fundamentally the same basic pattern of envenomation.

Several peptides isolated from Conus venoms have been characterized. These include the α-, μ- and ω-conotoxins which target nicotinic acetylcholine receptors, muscle sodium channels, and neuronal calcium channels, respectively (Olivera et al., 1985). Conopressins, which are vasopressin analogs, have also been identified (Cruz et al. 1987). In addition, peptides named conantokins have been isolated from *Conus geographus* and *Conus tulipa* (Mena et al., 1990; Haack et al., 1990). These peptides have unusual age-dependent physiological effects: they induce a sleep-like state in mice younger than two weeks and hyperactive behavior in mice older than 3 weeks (Haack et al., 1990). Recently, peptides named contryphans containing D-tryptophan residues have been isolated from *Conus radiatus* (U.S. Ser. No. 60/030,722), and bromo-tryptophan conopeptides have been isolated from *Conus imperialis* and *Conus radiatus* (U.S. Ser. No. 08/785,534).

Neuronal nicotinic acetylcholine receptors (nAChRs) are believed to be heteropentameric ion channel complexes generally requiring at least two different subunits (an α and a β). Molecular data indicate that in the mammalian central nervous system there exists a large number of different nAChR subunits. To date, seven different α subunits (α2–α7, α9) and three different β subunits (β2–β4) have been defined by cloning. The α3β4-containing nAChR subtype and the α3β2-containing nAChR subtype are each present in the autonomic nervous system and in the central nervous system. The α7-containing nAChR subtype is also present in the autonomic nervous system.

While postsynaptic nAChRs have been recognized for some time, more recent data have demonstrated the presence of presynaptic neuronal nAChRs. Agonist stimulation of presynaptic nAChRs induces neurotansmitter release. Nicotinic agonists have been shown to elicit the release of several different neurotransmitters, including dopamine from striatum and frontal cortex (El-Bizri and Clarke, 1994; Grady et al., 1992; Rapier et al., 1988); norepinephrine from hippocampus (Clarke and Reuben, 1996; Rowell and Winkler, 1984; Sacaan et al., 1995; Wilkie et al., 1993); glutamate from cortex, medial habenula nucleus and hippocampus (McGehee and Role, 1995; Vidal and Changeux, 1993; Gray et al, 1996); GABA from interpeduncular nucleus (Mulle et al., 1991) and acetylcholine for cortex and hippocampus (Lapchak et al., 1989; Rowell and Winkler, 1984).

In addition, it appears that distinct subtypes of presynaptic nAChRs regulate the release of different neurotransmitters. For example, nicotine-stimulated glutamate and acetylcholine release are blocked by α-bungarotoxin suggesting that these nAChRs include an α7 subunit (McGehee and Role, 1995). In contrast, nicotine-stimulated dopamine release is not blocked by α-bungarotoxin (Grady et al., 1992). Furthermore, the nAChRs modulating norepinephrine release pharmacologically differ from those modulating the release of glutamate, acetylcholine or dopamine (Clarke and Reuben, 1996; Sacaan et al., 1995).

As previously described, presynaptic nAChRs in the central nervous system (CNS) modulate the release of several neurotransmitters, including norepinephrine and dopamine (Wonnacott, 1997). CNS norepinephrine levels are important in the treatment and/or pathophysiology of mood disorders (Schatzberg and Nemeroff, 1995; Mongeau et al., 1997). CNS dopamine levels are important in addictive and psychotic disorders (Pontieri et al., 1996; Kahn and Davis, 1995). Thus, the possibility of selectively modulating the presynaptic release of specific neurotransmitters and the possibility of selectively targeting specific nAChRs has significant therapeutic applications. One example of a therapeutic application is tobacco addiction. Studies of nicotine self-administration in animal models suggest that block of nAChRs decreases the reinforcing properties of nicotine. Examples of therapeutic applications resulting from selectively targeting the nAChRs of the autonomic nervous system are the treatment of cardiovascular disorders, gastric mobility disorders and urinary incontinence.

It is desired to identify additional compounds which target different nAChR subtypes as well as the nAChR subtypes of the autonomic nervous system and the central nervous system. It is further desired to identify compounds which are useful as cardiovascular agents, gastric motility agents, urinary incontinence agents, anti-smoking agents, anti-cancer agents, anti-psychotic agents and anti-mood disorder agents.

SUMMARY OF THE INVENTION

This invention relates to uses of relatively short peptides about 14–17 residues in length, which are naturally available in minute amounts in the venom of the cone snails or analogs to the naturally available peptides, and which include two cyclizing disulfide linkages. More specifically, the present invention relates to the use of α-conotoxin peptides having the general formula $Xaa_1$-$Xaa_2$-Cys-Cys-$Xaa_3$-$Xaa_4$-Pro-$Xaa_5$-Cys-$Xaa_6$-$Xaa_7$-$Xaa_8$-$Xaa_9$-$Xaa_{10}$-$Xaa_{11}$-$Xaa_{12}$-Cys (SEQ ID NO:1)

for treating disorders regulated at neuronal nicotinic acetylcholine receptors. Such disorders include, but are not limited to, cardiovascular disorders, gastric motility disorders, urinary incontinence, nicotine addiction, mood disorders (such as bipolar disorder, unipolar depression, dysthymia and seasonal effective disorder) and small cell lung carcinoma, as well as the localization of small cell lung carcinoma In this formula, $Xaa_1$ is des-$Xaa_1$, Tyr, mono-iodo-Tyr or di-iodo-Tyr, $Xaa_2$ is any amino acid, $Xaa_3$ is any amino acid, $Xaa_4$ is any amino acid, $Xaa_5$ is any amino acid, $Xaa_6$ is any amino acid, $Xaa_7$ is any amino acid, $Xaa_8$ is a ny amino acid, $Xaa_9$ is des-$Xaa_9$ or any amino acid, $Xaa_{10}$ is des-$Xaa_{10}$ or any amino acid, $Xaa_{11}$ is des-$Xaa_{11}$ or any amino acid and $Xaa_{12}$ is des-$Xaa_{12}$ or any amino acid, with the proviso that when the disorder is small cell lung carcinoma, then the α-conotoxin peptide is not a peptide having an amino acid sequence set forth in SEQ ID NO:2 or SEQ ID NO:13. Disulfide linkages exist between the first and third cysteines and the second and fourth cysteines. Pro may be replaced with hydroxy-Pro. The C-terminus may contain a hydroxyl or an amide group, preferably an amide group.

SUMMARY OF THE SEQUENCE LISTING

Figure 1:
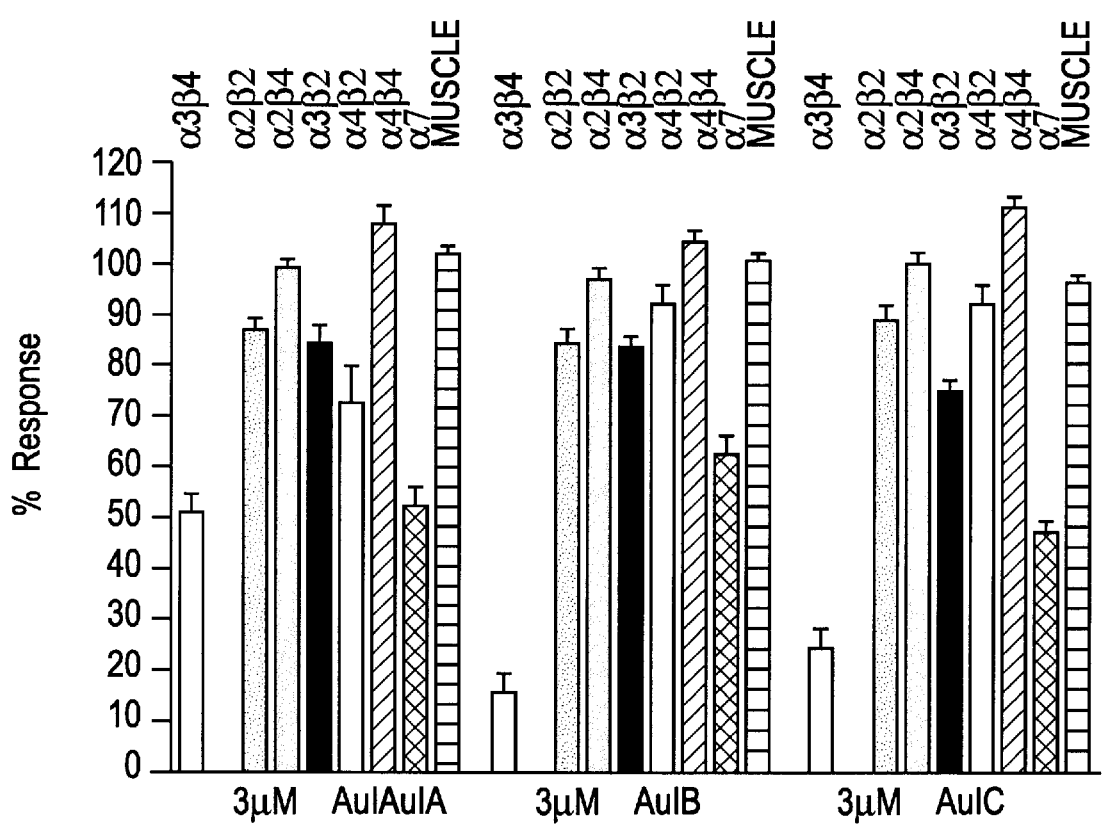
FIG. 1 shows the selectivity of 3 $\mu$M α-conotoxins AuIA, AuIB and AuIC on nAChRs expressed in oocytes.

SEQ ID NO:1 is the generic formula for the α-conotoxin peptides useful for the present invention. SEQ ID NO:2 is α-conotoxin peptide MII. SEQ ID NO:3 is α-conotoxin peptide Tyr-MII. SEQ ID NO:4 is α-conotoxin peptide FAT-MII (MII with FAT at residues 9–11 instead of HLE in MII). SEQ ID NO:5 is α-conotoxin peptide AuIA. SEQ ID NO:6 is α-conotoxin peptide Tyr-AuIA. SEQ ID NO:7 is α-conotoxin peptide AuIB. SEQ ID NO:8 is α-conotoxin peptide AuIC. SEQ ID NO:9 is α-conotoxin peptide PnIA. SEQ ID NO:10 is α-conotoxin peptide PnIA A10L (PNIA with L at residue 10 instead of A in PnIA). SEQ ID NO:11 is α-conotoxin peptide PnIA N11S (PnIA with S at residue 11 instead of N in PnIA). SEQ ID NO:12 is α-conotoxin peptide PnIB. SEQ ID NO:13 is α-conotoxin peptide ImI.

DETAILED DESCRIPTION OF THE PREFERRED EMBODIMENT

This invention relates to uses of relatively short peptides about 14–17 residues in length, which are naturally available in minute amounts in the venom of the cone snails or analogs to the naturally available peptides, and which include two cyclizing disulfide linkages. More specifically, the present invention relates to the use of α-conotoxin peptides having the general formula $Xaa_1$-$Xaa_2$-Cys-Cys-$Xaa_3$-$Xaa_4$-Pro-$Xaa_5$-Cys-$Xaa_6$-Cys (SEQ ID NO:1)

for treating disorders regulated at neuronal nicotinic acetylcholine receptors. Such disorders include, but are not limited to, cardiovascular disorders, gastric motility disorders, urinary incontinence, nicotine addiction, mood disorders (such as bipolar disorder, unipolar depression, dysthymia and seasonal effective disorder) and small cell lung carcinoma, as well as the localization of small cell lung carcinoma. In this formula, $Xaa_1$ is des-$Xaa_1$, Tyr, mono-iodo-Tyr or di-iodo-Tyr, $Xaa_2$ is any amino acid, $Xaa_3$ is any amino acid, $Xaa_4$ is any amino acid, $Xaa_5$ is any amino acid and $Xaa_6$ represents a peptide of 3–7 amino acids, with the proviso that when the disorder is small cell lung carcinoma, then the α-conotoxin peptide is not a peptide having an amino acid sequence set forth in SEQ ID NO:2 or SEQ ID NO:13. Disulfide linkages exist between the first and third cysteines and the second and fourth cysteines. Pro may be replaced with hydroxy-Pro. The C-terminus may contain a carboxyl or an amide group, preferably an amide group. The amino acid or the amino acid residues of the peptides is an α-amino acid, which includes natural amino acids, including unusual amino acids such as γ-carboxyglutamic acid, as well as modified or non-natural amino acids, such as those described in, for example, Roberts et al. (1983).

Examples of α-conotoxin peptides falling within the generic formula are set forth in Table 1. These conotoxin peptides are members of the α4 subclass of α-conotoxin peptides. The tyrosine residue at the N-terminus can also be added to the other peptides shown in Table 1. This tyrosine residue can be iodinated to contain 1 or 2 iodines. In addition, the proline residues can be replaced by hydroxyproline. The tryptophan residue may be replaced by bromotryptophan. These changes to the peptides do not change the activity of the native peptide.

TABLE 1

| #-Conotoxin Peptides | | |
|---|---|---|
| Peptide | Sequence | SEQ ID NO: |
| MII | GCCSNPVCHLEHSNLC | 2 |
| Tyr-MII | YGCCSNPVCHLEHSNLC | 3 |
| FAT-MII | GCCSNPVCFATHSNLC | 4 |
| AuIA | GCCSYPPCFATNSDYC | 5 |
| Tyr-AUIA | YGCCSYPPCFATNSDYC | 6 |
| AuIB | GCCSYPPCFATNSD-C | 7 |
| AuIC | GCCSYPPCFATNSGYC | 8 |
| PnIA | GCCSLPPCAANNPDYC | 9 |
| PnIA A10L | GCCSLPPCALNNPDYC | 1D |
| PnIA N11S | GCCSLPPCAASNPDYC | 11 |
| PnIB | GCCSLPPCALSNPDYC | 12 |
| ImI | GCCSDPRCA---W-RC | 13 |

Additional peptides falling within the general formula can be made based on the peptides shown in Table 1 by making analogs of these peptides or by making conservative substitutions for the amino acid residues shown in Table 1. For example, a FAT-PnIA analog can be made in which FAT replaces AAN at residues 9–11. Conservative substitutions are well known in the art and include, for example, the change of (or vice versa): alanine to serine; arginine to lysine; asparagine to glutamine or histidine; aspartate to glutamate; cysteine to serine; glycine to proline; isoleucine to leucine or valine; methionine to leucine or isoleucine; phenylalanine to tyrosine, leucine or methionine; serine to threonine; tryptophan to tyrosine. Changes in these peptides can be made in view of the teachings set forth in U.S. provisional patent application Nos. 60/062,783 and 60/065,814 and in U.S. patent application No. 09/177,626.

The α-conotoxin peptides of the general formula are active on the α3β4, α3β2 or α7 containing subtypes of nAChRs which are present in the autonomic and central nervous systems. For example, the α3β4-containing subtype is present in sympathetic ganglia and the central nervous system. Similarly, the α3β2-containing subtype is present in sympathetic ganglia and the central nervous system. Finally, the α7-containing subtype is present at peripheral ganglia and in the central nervous system. Thus, they are useful as cardiovascular agents, gastric motility agents, urinary incontinence agents, anti-smoking agents and for the treatment or localization of small cell lung carcinoma. These peptides are also useful for treating psychosis, pain and spastic disorders. Finally, these peptides are useful for treating mood disorders.

The α-conotoxin peptides can be designed to be more specific for one of these subtypes of nAChRs. For example, MIl has a higher specificity for the α3β2-containing subtype, whereas FAT-MII has a higher specificity for the α3β2-containing subtype. Similarly, PnIA has a higher specificity for the α3β2-containing subtype, whereas PnIA A10L has a higher specificity for the α7-containing subtype. The peptides set forth in Table 1 have the following specificities (with respect to higher specificity, generally by several orders of magnitude): α3β2-cortaining subtype: MII, Tyr-MII, PnIA and PnIA N11S; α3β4-containing subtype: AuIA, AuIB, AuIC, FAT-MII and Tyr-FAT-MII; and, α7-containing subtype: PnIB, ImI and PnIA A10L. The specificity of each peptide is readily determined by assaying for subtype specificity in accordance with techniques well known in the art.

These peptides are sufficiently small to be chemically synthesized. General chemical syntheses for preparing the foregoing conopeptides peptides are described hereinafter, along with specific chemical synthesis of conopeptides and indications of biological activities of these synthetic products. Various ones of these conopeptides can also be obtained by isolation and purification from specific Conus species using the technique described in U.S. Pat. No. 4,447,356 (Olivera et al., 1984), the disclosure of which is incorporated herein by reference.

Although the native conopeptides can be obtained by purification from cone snails, because the amounts of conopeptides obtainable from individual snails are very small, the desired substantially pure conopeptides are best practically obtained in commercially valuable amounts by chemical synthesis using solid-phase strategy. For example, the yield from a single cone snail may be about 10 micrograms or less of conopeptide. By "substantially pure" is meant that the peptide is present in the substantial absence of other biological molecules of the same type; it is preferably present in an amount of at least about 85% purity and preferably at least about 95% purity. Chemical synthesis of biologically active conopeptides depends of course upon correct determination of the amino acid sequence. Thus, the conopeptides of the present invention may be isolated, synthesized and/or substantially pure.

The conopeptides can also be produced by recombinant DNA techniques well known in the art. Such techniques are described by Sambrook et al. (1979). Nucleic acid sequences coding for the α-conotoxin peptides and α-conotoxin propeptides can be isolated and cloned using conventional techniques. Alternatively, nucleic acid sequences coding for the α-conotoxin peptides can be synthesized on the basis of the amino acid sequences of the peptides disclosed herein and the known degeneracy of the genetic code. The nucleic acids for the peptides can be designed to achieve maximal expression in a given host system. The peptides produced in this manner are isolated, reduced if necessary, and oxidized to form the correct disulfide bonds, if present in the final molecule.

One method of forming disulfide bonds in the conopeptides of the present invention is the air oxidation of the linear peptides for prolonged periods under cold room temperatures or at room temperature. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent conopeptide molecule. However, because of the dilution resulting from the presence of other fractions of less biopotency, a somewhat higher dosage may be required.

The peptides are synthesized by a suitable method, such as by exclusively solid-phase techniques, by partial solid-phase techniques, by fragment condensation or by classical solution couplings.

In conventional solution phase peptide synthesis, the peptide chain can be prepared by a series of coupling reactions in which constituent amino acids are added to the growing peptide chain in the desired sequence. Use of various coupling reagents, e.g., dicyclohexylcarbodiimide or diisopropylcarbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (1974). Techniques of exclusively solid-phase synthesis are set forth in the textbook, "Solid-Phase Peptide Synthesis," (Stewart and Young, 1969), and are exemplified by the disclosure of U.S. Pat. No. 4,105,603 (Vale et al., 1978). The fragment condensation method of synthesis is exemplified in U.S. Pat. No. 3,972,859 (1976). Other available syntheses are exemplified by U.S. Pat. No. 3,842,067 (1974) and U.S. Pat. No. 3,862,925 (1975). The synthesis of peptides containing γ-carboxyglutamic acid residues is exemplified by Rivier et al. (1987), Nishiuchi et al. (1993) and Zhou et al. (1996).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chain protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or para-methylbenzhydrylamine (MBHA) resin. Preparation of the hydroxymethyl resin is described by Bodansky et al. (1966). Chloromethylated resins are commercially available from Bio Rad Laboratories (Richmond, Calif.) and from Lab. Systems, Inc. The preparation of such a resin is described by Stewart and Young (1969). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (Kornreich et al., 1986) can be used, or should still other groups than the free acid be desired at the C-terminus, it may be preferable to synthesize the peptide using classical methods as set forth in the Houben-Weyl text (1974).

The C-terminal amino acid, protected by Boc or Fmoc and by a side-chain protecting group, if appropriate, can be first coupled to a chloromethylated resin according to the procedure set forth in Horiki et al. (1978), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder and Lubke (1 965).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC, DIC, HBTU, HATU, TBTU in the presence of HoBt or HoAt).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder and Lubke (1965) and Kapoor (1970).

Each protected amino acid or amino acid sequence is introduced into the solid-phase reactor in about a twofold or more excess, and the coupling may be carried out in a medium of dimethylformamide (DMF):$CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (1970). Coupling reactions can be performed automatically, as on a Beckman 990 automatic synthesizer, using a program such as that reported in Rivier et al. (1978).

After the desired amino acid sequence has been completed, the intermediate peptide can be removed from the resin support by treatment with a reagent, such as liquid hydrogen fluoride or TFA (if using Fmoc chemistry), which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride or TFA for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptidoresin, to create bonds between Cys residues. To effect such a disulfide cyclizing linkage, fully protected peptide can be cleaved from a hydroxymethylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA) resin or a methylbenzhydrylamine (MBHA), can take place at 0° C. with hydrofluoric acid (HF) or TFA, followed by oxidation as described above.

The present α-conotoxins block α3β4-containing nAChRs, α3β2-containing nAChRs or α7-containing nAChRs expressed in Xenopus oocytes, as noted above. The present α-conotoxins also block other nAChR subunit combinations but with much lower affinities. For example, at low submicromolar concentrations, e.g., 0.3–1.0 μM, the AuIA blocks essentially only α3β4-containing receptors (copending application Ser. No. 08/857,068, incorporated herein by reference). It is also known that α-conotoxin MII blocks native α3β2-containing nAChRs and α3β4-containing nAChRs (copending application Ser. No. 08/761,674, incorporated herein by reference).

A particular advantage of α-conotoxin antagonists is their ability to discriminate between nonsymmetrical ligand binding interfaces present on the receptor. The best-studied example is α-conotoxin MI binding to the muscle nicotinic receptor. In mouse muscle, α-conotoxin MI displays a four order-of-magnitude selectivity for the α1/δ vs. the α1/γ binding site (Sine and Claudio, 1991). Nevertheless, α-conotoxin MI functionally blocks the muscle receptor with affinity comparable to its affinity for the α1/δ binding site, indicating that only one toxin molecule is required to prevent channel activation (Martinez et al., 1995). It was also recently demonstrated that α-conotoxin MII has two binding sites on α3β2-containing and α3β4-containing receptors expressed in Xenopus oocytes and only one toxin molecule is required to block function (Cartier et al., 1996b). α-Conotoxin MII discriminates between the α3β2-containing and α3β4-containing interface by four orders-of-magnitude (see Ser. No. 08/761,674). Thus, α-conotoxin MII's has the ability to potently block any receptor containing an α3β2-containing subunit interface regardless of what other α and β subunits may be present in the receptor complex. α-Conotoxin MII's potency at such receptors would still be high. Similarly, the α-conotoxins AuIA, AuIB and AuIC, have the ability to discriminate between the α3β4-containing and α3β2-containing interface (see Ser. No. 08/857,068). Consequently, AuIA, AuIB and AuIC have the ability to potently block any receptor containing an α3β4-containing subunit interface regardless of what other α and β subunits may be present in the receptor complex. These α-conotoxins' potency at such receptors would still be high. Similarly, ImI shows higher specificity to the α7-containing subunit.

Peptide analogs and peptide mimetics which are specific for the noted subtypes of the nAChR are prepared on the basis of the teachings disclosed herein as well as the teachings presented in the provisional patent application Ser. No. 60/065,814 using conventional drug modeling, drug design and combinatorial chemistry. Suitable techniques include, but are not limited to those described in U.S. Pat. No. 5,571,698, WO 95/21193, Ecker and Cook (Bio/Technology 13:351–360 (1995), Persidis and Persidis (*Bio/Technology* 15:1035–1036 (1997)), Johnson et al. ("Peptide Turn Mimetics" in *Biotechnology and Pharmacy*, Pezzato et al., eds., Chapman and Hall, New York (1993)), Sun and Cohen (Gene 137:127–132 (1993)) and the references cited therein. the development of peptide analogs and peptide mimetics are prepared using commercially available drug design software, including those set forth in the Persidis and Persidis reference. These peptide analogs and peptide mimetics have the same activities as the α-conotoxins described herein and in the published literature. As described herein, the specificity of an individual α-conotoxin can be changed by making a peptide analog. The specificity of the peptide analog is determined by using nAChR subtype assays, such as described herein.

Peptide analogs and derivatives can be made in accordance with conventional techniques. Suitable techniques for peptide synthesis is described in U.S. Pat. No. 5,514,774, as well as the references cited therein. Peptide niimetics are similarly synthesized by conventional techniques.

Pharmaceutical compositions containing a compound of the present invention as the active ingredient can be prepared according to conventional pharmaceutical compounding techniques. See, for example, *Remington's Pharmaceutical Sciences*, 18th Ed. (1990, Mack Publishing Co., Easton, Pa.). Typically, an antagonistic amount of the active ingredient will be admixed with a pharmaceutically acceptable carrier. The carrier may take a wide variety of forms depending on the form of preparation desired for administration, e.g., intravenous, oral or parenteral. The compositions may further contain antioxidizing agents, stabilizing agents, preservatives and the like.

For oral administration, the compounds can be formulated into solid or liquid preparations such as capsules, pills, tablets, lozenges, melts, powders, suspensions or emulsions. In preparing the compositions in oral dosage form, any of the usual pharmaceutical media may be employed, such as, for example, water, glycols, oils, alcohols, flavoring agents, preservatives, coloring agents, suspending agents, and the like in the case of oral liquid preparations (such as, for example, suspensions, elixirs and solutions); or carriers such as starches, sugars, diluents, granulating agents, lubricants, binders, disintegrating agents and the like in the case of oral solid preparations (such as, for example, powders, capsules and tablets). Because of their ease in administration, tablets and capsules represent the most advantageous oral dosage unit form, in which case solid pharmaceutical carriers are obviously employed. If desired, tablets may be sugar-coated or enteric-coated by standard techniques. The active agent can be encapsulated to make it stable to passage through the gastrointestinal tract while at the same time allowing for passage across the blood brain barrier. See for example, WO 96/11698.

For parenteral administration, the compound may be dissolved in a pharmaceutical carrier and administered as either a solution or a suspension. Illustrative of suitable carriers are water, saline, dextrose solutions, fructose solutions, ethanol, or oils of animal, vegetative or synthetic origin. The carrier may also contain other ingredients, for example, preservatives, suspending agents, solubilizing agents, buffers and the like. When the compounds are being administered intrathecally, they may also be dissolved in cerebrospinal fluid.

The active agents, which are peptides, can also be administered in a cell based delivery system in which a DNA sequence encoding an active agent is introduced into cells designed for implantation in the body of the patient, especially in the spinal cord region. Suitable delivery systems are described in U.S. Pat. No. 5,550,050 and published PCT application Ser. Nos. WO 92/19195, WO 94/25503, WO 95/01203, WO 95/05452, WO 96/02286, WO 96/02646, WO 96/40871, WO 96/40959 and WO 97/12635. Suitable DNA sequences can be prepared synthetically for each active agent on the basis of the developed sequences and the known genetic code.

The use of α-conotoxin peptides for the treatment or localization of small cell lung carcinoma is disclosed in U.S. Pat. No. 5,595,972, incorporated herein by reference. The use of α-conotoxin peptides for treating cardiovascular disorders is disclosed in international application PCT/US97/20669 designating the U.S., incorporated herein by reference. The use of α-conotoxin peptides for treating nicotine addiction, psychosis and mood disorders is disclosed in U.S. application Ser. No. 08/761,674, incorporated herein by reference. α-Conotoxin peptides with specificity for the α3β2 nAChRs are particularly preferred for treating nicotine addiction. α-Conotoxin peptides with specificity for the α3β4 nAChRs are particularly preferred for treating mood disorders. Gastric motility disorders and urinary incontenence are treated in conventional manner using an antagonistic amount of α-conotoxin peptides disclosed herein.

The α-conotoxin peptides are administered in an amount sufficient to antagonize the α3β4, α3β4 or α7 nAChRs as noted above. The dosage range at which the conotoxin peptides exhibit this antagonistic effect can vary widely depending upon the particular condition, e.g., cardiovascular disorders, gastric motility disorders, urinary incontinence, nicotine addiction, mood disorders or small cell lung carcinoma, being treated, the severity of the patient's condition, the patient, the specific conotoxin being administered, the route of administration and the presence of other underlying disease states within the patient Typically the conopeptides of the present invention exhibit their therapeutic effect at a dosage range from about 0.05 mg/kg to about 250 mg/kg, and preferably from about 0.1 mg/kg to about 100 mg/kg of the active ingredient. A suitable dose can be administered in multiple sub-doses per day. Typically, a dose or sub-dose may contain from about 0.1 mg to about 500 mg of the active ingredient per unit dosage form. A more preferred dosage will contain from about 0.5 mg to about 100 mg of active ingredient per unit dosage form. Dosages are generally initiated at lower levels and increased until desired effects are achieved.

The iodinated analogs of the α-conotoxin peptides can also be used for receptor mapping using conventional techniques. These iodinated analogs can also be used to screen for additional α-conotoxin peptides or other compounds which have specificity for the α3β4, α3β2 or α7 subtypes of nAChRs using conventional techniques. One suitable technique involves competitive binding or displacement of the peptide or compound in question with, for example, MII. Peptides or compounds identified in this manner will have the same activity as the compounds used for the screening assay.

EXAMPLES

The present invention is described by reference to the following Examples, which are offered by way of illustration and are not intended to limit the invention in any manner. Standard techniques well known in the art or the techniques specifically described below were utilized.

Example 1
Chemical Synthesis of α-Conotoxins From *Conus aulicus*

The synthesis of AuIA, AuIB and AuIC conopeptides was separately performed using conventional protection chemistry as described by Cartier et al., 1996a. Briefly, the linear chains were built on Rink amide resin by Fmoc procedures with 2-(1H-benzotriol-1-yl)-1,1,3,3,-tetramethyluronium tetrafluoroborated coupling using an ABI model 430A peptide sythesizer with amino acid derivatives purchased from Bachem (Torrence Calif.). Orthogonal protection was used on cysteines: $Cys^3$ and $Cys^{16}$ were protected as the stable Cys(S-acetamidomethyl), while $Cys^2$ and $Cys^8$ were protected as the acid-labile Cys(S-trityl). After removal of the terminal Fmoc protecting group and cleavage of the peptides from the resins, the released peptides were precipitated by filtering the reaction mixture into −10° C. methyl t-butyl ether, which removed the protecting groups except on $Cys^3$ and $Cys^{16}$. The peptides were dissolved in 0.1% TFA and 60% acetonitrile and purified by RPLC on a Vydac $C_{18}$ preparative column (22×250 mm) and eluted at a flow rate of 20 mL/min with a gradient of acetonitrile in 0.1% TFA.

The disulfide bridges in the three conopeptides were formed as described in Cartier et al. (1996a). Briefly, the disulfide bridges between $Cys^2$ and $Cys^8$ were formed by air oxidation which was judged to be complete by analytical RPLC. The monocyclic peptides were purified by RPLC on a Vydac $C_{18}$ preparative column (22×250 mm) and eluted with a gradient of acetonitrile in 0.1% TFA. Removal of S-acetamidomethyl groups and closure of the disulfide bridge between $Cys^3$ and $Cys^{16}$ was carried out simultaneously be iodine oxidation. The cyclic peptides were purified by RPLC on a Vydac $C_{18}$ preparative column (22×250 mm) and eluted with a gradient of acetonitrile in 0.1% TFA.

Example 2
Biological Activity of α-Conotoxins From *Conus aulicus*

Each of the AuIA, AuIB and AuIC conopeptides were tested for activity on neuronal nAChRs in *Xenopus laevis* oocytes containing different subtypes of nAChRs as described by Cartier et al. (1996a). Briefly, oocytes were injected with RNA encoding the various α and β subunits of rat nAChRs and incubated at 25° C. for 1–9 days prior to use. Electrophysiological currents were measured using conventional techniques, such as described in Cartier et al. (1996a). Measurements were made for oocytes perfused with acetylcholine as controls and for oocytes incubated with 3 μM of either AuIA conopeptide, AuIB conopeptide or AuIC conopeptide followed by perfusion with acetylcholine. Each of these conopeptides was active on neuronal nAChRs with a preference for nAChRs of the α3β4 subtype. AuIB was found to be the most potent and selective of the three for the α3β4 subtype. The biological activity of these peptides against the panel of nAChR subtypes is shown in FIG. 1.

Example 3
Synthesis of Iodinated Tyr-MII

Tyr-MII was prepared in accordance with the procedure of Example 1. Iodination of the Tyr-MII was preformed by the Chloramine T method. Briefly, excess peptide was mixed with NaI (either radioactive or nonradioactive version). Chloramine T was then added to initiate the iodination process. Procedure was carried out at a somewhat acidic pH (5.3) to selectively iodinate the Tyr (instead of the His which can also be iodinated at basic pH). Reaction was terminated by the addition of excess ascorbic acid. Mono-iodo and di-iodo Tyr-MII were purified from unmodified peptide using RPLC. The mono- and di-iodo peptides both retain activity as measured by antagonist activity on nAChRs expressed in Xenopus oocytes, with a preference for the α3β2 subtype.

Example 4
Synthesis and Activity of FAT-MII

FAT-MII was prepared in accordance with the procedure of Example 1 and its activity was measured in accordance with the procedure of Example 2. While MII shows a preference for the α3β2 subtype, FAT-MII shows a preference for the α3β4 subtype.

Example 5
Synthesis and Activity of PnIA Analogs

Figure 2:
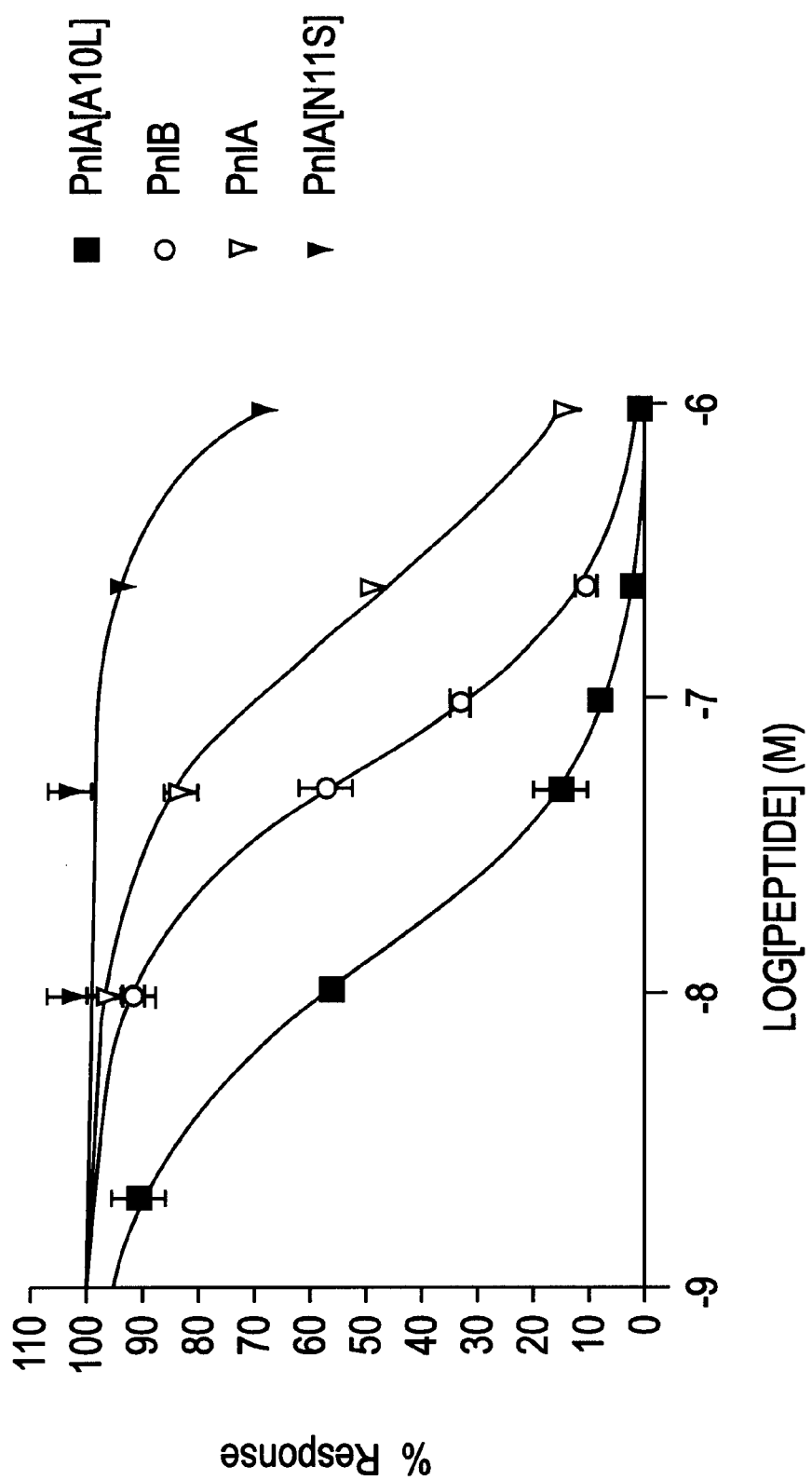
FIG. 2 shows the antagonistic activity of PnIA (△), PnIB (○), PnIA A10L (■) and PnIA N11S (▼) with respect to the α7 subtype of neuronal nicotinic acetylcholine receptors.

PnIA A10L and PnIA N11S were prepared in accordance with the procedure of Example 1 and their activities were measured in accordance with the procedure of Example 2. The antagonistic activity of these peptides as well as peptides PnIA and PnIB for the α7 subtype is shown in FIG. 2. FIG. 2 shows that PnIA A10L has ahigher affinity to the α7 subtype than PnIB which shows preference to this subtype. PnIA shows preference to the α3β2 subtype. The $IC_{50}$ (in nmol) for each peptide with respect to α7 nAChR is as follows: PnIA N11S: 1705; PnIA: 229; PnIB: 61; and PnIA A10L: 12.

Example 6

The Effects of α-Conotoxin MII on Nicotine-stimulated [$^3$H]-Dopamine Release

The ability of α-conotoxin MII to block nicotine-evoked [$^3$H]-dopamine release was assessed using rat striatal synaptosomes as described in U.S. Ser. No. 08/761,764 or PCT/US97/22350. Three μM nicotine stimulates the release of [$^3$H]-dopamine. This release is fully blocked by the non-selective, noncompetitive antagonist mecamylamine. The release is abolished in the absence of external calcium. (−)-Nicotine has previously been shown to increase [$^3$H]-dopamine release from rat striatal synaptosomes in a concentration-dependent manner with an estimated $EC_{50}$ of $1.6 \times 10^{-7}$ M (El-Bizri and Clarke, 1994). α-Conotoxin MII blocked 3 μM nicotine-stimulated [$^3$H]-dopamine release with a nonsignificant trend toward block at 0.1 nM (P=0.08). At concentrations of 1 nM and above, α-conotoxin significantly blocked nicotine-evoked [$^3$H]-dopamine release in a dose-dependent manner. Concentrations of α-conotoxin MII of 10 nM and below are expected to be specific for α3β2 receptors ($IC_{50}$ 0.5 nM), whereas concentrations of 100 nM and 1 μM may have measurable effects on other nAChR subtypes (Cartier et al., 1996a; Cartier et al., 1996b).

Example 7

Effects of α-Conotoxin MII on Depolarization-stimulated [$^3$H]-Dopamine Release To further investigate the specificity of effects of α-conotoxin MII, its effects on KCl-induced dopamine release were assessed. One hundred nM α-conotoxin MII, a concentration which blocks 33% of nicotine stimulated dopamine release, had no effect on potassium-stimulated dopamine release.

Example 8

Effects of α-Conotoxin MII on 100 μM Nicotine-stimulated [$^3$H]-Dopamine Release Previous investigators who have examined the effects of κ-bungarotoxin on nicotine-stimulated dopamine release have reported variable effects. One group reported a 50% inhibition of striatal dopamine release by 100 nM κ-bungarotoxin (Wonnacott et al., 1995). Other investigators have reported complete block of striatal dopanrine release by 100 nM κ-bungarotoxin (Grady et al., 1992; Wilkie et al., 1993; Schultz and Zigmond, 1989). One difference between these studies is that the investigators who observed a 50% inhibition used 3 μM nicotine whereas the investigators who observed complete block used 50 or 100 μM nicotine. It has been suggested that at 3 μM, nicotine could be acting on a higher-affinity nicotinic receptor that has low sensitivity to κ-bungarotoxin whereas 50 to 100 μM nicotine is acting on a lower-affinity nAChR which has a high sensitivity to κ-bungarotoxin (Wonnacott et al., 1995). To more fully compare our results with previously reported results with κ-bungarotoxin, the effects of α-conotoxin MII on 160 nM, 3 μM and 100 μM-stimulated dopamine release were tested. One hundred nM α-conotoxin MII blocks 44% of 100 μM nicotine-stimulated [$^3$H]-dopamine release compared to 34% of 3 μM nicotine and 50% of 160 nM nicotine stimulated [$^3$H]-dopamine release.

Example 9

Effects of α-Conotoxin MII on Nicotine-stimulated Norepinephrine Release

Nicotine evokes the release of [$^3$H]-norepinephrine in hippocampus. It has previously been reported that nicotine releases striatal dopamine more potently than hippocampal norepinephrine ($EC_{50}$=0.16 μM vs. 6.5 μM) in synaptosomal preparations (Clarke and Reuben, 1996). Three μM nicotine was utilized to maximize the chance of seeing an effect by the competitive antagonist α-conotoxin MII. One hundred nM α-conotoxin MII blocked 0% of nicotine-stimulated norepinephrine release which was not statistically different from control. In contrast, 1 μM α-conotoxin MII blocked 45% (FIG. 4). α-Conotoxin MII was also tested on 100 μM nicotine-stimulated release. One hundred nM MII blocked 11% and 1 μM blocked 24%.

Example 10

Experimental Procedures for Analysis of Effects of α-Conotoxin AuIB

Materials: [$^3$H]-Dopamine (dihydroxyphenyl-ehtylamine, 3,4[7-$^3$H]-) (~30 Ci/mmol) and [$^3$H]-norepinephrine (norepinephrine, levo-[ring-2,5,6-[$^3$H]-) (~42 Ci/mmol) were purchased from Dupont NEN, Boston, Mass. [$^3$H]-Radioligands were distributed into 5 and 14.1 μCi aliquots respectively and stored under argon at −80° C. (−)Nicotine hydrogen tartrate was from Sigma. Pargyline HCl and mecamylamine HCl were from Research Biochemicals International. Prior to use, all drugs were prepared fresh in superfusion buffer (SB) consisting of 128 mM NaCl, 2.4 mM KCl, 3.2 mM $CaCl_2$, 1.2 mM $KH_2PO_4$, 0.6 mM $MgSO_4$, 25 mM HEPES, 10 mM D-glucose, 1 nM L-ascorbic acid, 0.1 mM pargyline, 0.1 mM BSA with the pH adjusted to 7.5 with NaOH.

Animals: Male Sprague-Dawley rats, weighing 200–400 g, were maintained on a 12/12 h light/dark cycle. Rats were drug-naive and housed three per cage, and food and water were available ad libitum.

Synaptosomal Preparation and [$^3$H]-Radioligand Preloading: Synaptosomes were prepared as previously described (Kulak et al., 1997). A crude P2 synaptosomal fraction was resuspended in SB (0.5 ml/100 mg wet tissue weight) containing 0.12 μM [$^3$H]-dopamine for striatal tissue or 0.2 μM [$^3$H]-norepinephrine for hippocampal tissue and incubated at 37° C. for 10 min. The loaded synaptosomes were centrifuged at 1000 g for 5 min at room temperature (24° C.), and the pellet was gently resuspended in 2.0 ml of SB. The high [$K^+$]-stimulated release solution was SB in which the [$K^+$] was elevated to 22.4 mM and the [$Na^+$] was decreased to 108 mM.

Superfusion: The assay system was as previously described (Kulak et al., 1997). Briefly, the system had twelve identical channels connected to a pump which continuously pulled the superfusate through individual filter holders containing the synaptosomes at a rate of 0.5 ml/min. Teflon® TFE tubing and Teflon®-coated parts were used upstream of the synaptosomes to avoid plasticizers such as Tinuvin 770 (a common light and UV radiation stabilizer used in a wide range of plastics) known to block neuronal nAChRs (Papke et al., 1994).

Following a preliminary superfusion period of 13 minutes for assays containing α-conotoxin AuIB or 31 minutes for all other toxins, a 1 min (0.5 ml) pulse of synaptosomal buffer with or without agonist was delivered simultaneously to all channels by switching on solenoids. Nicotine concentration was 3 μM in dopamine-release experiments and 100 μM in norepinephrine-release experiments. Two-minute fractions per channel were collected in polypropylene mini-vials containing 4.0 ml of scintillation fluid. Following the collection period, the filters holding the synaptosomes were removed to determine the residual radioactivity. A liquid scintillation counter (Beckman LS9800, 57.2% efficiency) was used to determine tritium levels.

Data Analysis: It has previously been shown that tritium released by nAChR agonists or b depolarizing concentrations of KCl is directly proportional to total radioligand released (Rapier et al., 1988). Thus, levels of tritium released is assumed to correspond directly to amount of radioligand released.

Release is calculated as: (dpm in the peak fractions—baseline release)/baseline release. Baseline release is defined as the average of two pre- and two post-release fractions. Release is normalized as a percentage of total agonist-stimulated release. Agonist-stimulated release with superfusate containing different α-conotoxin concentrations were compared to those of controls without toxin and analyzed for statistically significant mean differences using a t-test on raw (non-normalized) data with SPSS software (SPSS, Chicago, Ill.).

Example 11

Effects of α-Conotoxin AuIB on Nicotine-stimulated Norepineprrine Release

Figure 3A:
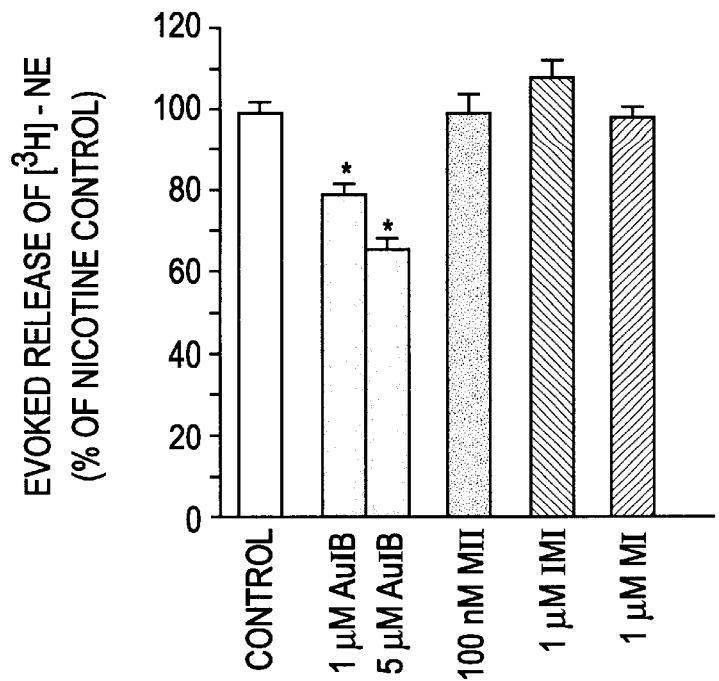
FIGS. 3A and 3B show the effects of α-conotoxins on nicotine-stimulated release of norepinephrine from rat hippocampal synaptosomes (3A) or dopamine from rat striatal synaptosomes (3B). *P≦0.001. Data are from 3–10 experiments with 3–6 replicates within each experiment.
Figure 3B:
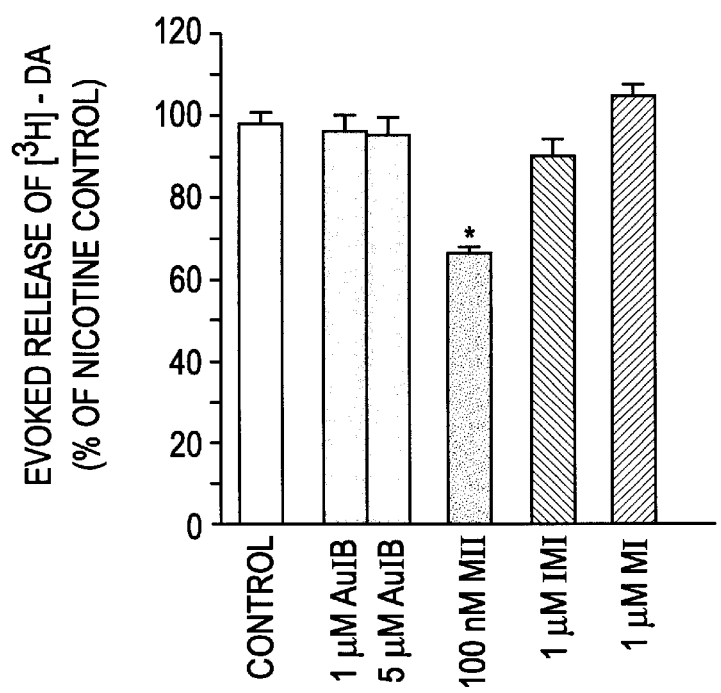

Presynaptic nicotinic receptors are known to be involved in the release of various neurotransmitters including norepinephrine and dopamine. The effects of α-conotoxin AuIB and other α-conotoxins were assessed in this regard. Nicotine-stimulated norepinephrine or dopamine release was analyzed using synaptosomes from rat hippocampus or from rat striatum, respectively. AuIB at 1 and 5 μM block a portion of nicotine-stimulated norepinephrine release but not that of dopamine release. The converse result is obtained using the α3β2 selective α-conotoxin MII. MII blocks nicotine-stimulated dopamine release but has no effect on nicotine-stimulated norepinephrine release. In addition, it was found that the α7 selective α-conotoxin ImI and α1 selective MI all fail to block nicotine-stimulated norepinephrine release. Similarly, it was found that ImI and MI also fail to block nicotine-stimulated release of dopamine. These results are shown in FIGS. 3A and 3B. The significance of this data is as follows: (a) norepinephrine release: 1 μM AuIB, p=0.001; 5 μM AuIB, p<0.001; MII, p=0.75; ImI, p=0.64; MI, p=0.5; (b) dopamine release: 1 μM AuIB, p=0.93; 5 μM AuIB, p=0.68; MII, p<0.001; ImI, p=0.24; MI, p=0.85.

The specificity of α-conotoxin AuIB's block of norepinephrine release was further assessed by testing its effects on high [K$^+$]-induced norepinephrine release. Hippocampal synaptosomes were loaded with [$^3$H]-norepinephrine and pre-incubated with or without α-conotoxin AuIB. Synaptosomes were subsequently depolarized with a one minute pulse of synaptosomal buffer that contained high K$^+$ with or without AuIB. Concentrations of AuIB which significantly block nicotine-stimulated norepinephrine release had no effect on depolarization-stimulated norepinephrine release. One μM AuIB responses=92.2±3.7%, p=0.5; 5 μM AuIB response=99.0±4.6%, p=0.95.

Example 12

Inhibition of SCLC Proliferation by α-Conotoxins

Small cell lung carcinoma (SCLC) cells have been found to express cholinergic nicotinic receptors (Maneckjee et al., 1990; Chini et al., 1992; Tarroni et al., 1992; Schuller et al., 1990). These SCLC nicotinic receptors have been shown to be of neuronal type (Chini et al., 1992; Tarroni et al., 1992). Nicotine and cytosine each stimulate the release of 5-hydroxytryptamine (5HT or serotonin) which acts as a potent mitogen in SCLC cells (Maneckjee et al., 1990; Cattaneo et al., 1993). α-Conotoxin MI has been found to block the nicotine or cytosine induced release of serotonin and at a concentration of 1 μM it completely antagonized the nicotine and cytosine stimulation of SCLC proliferation (Codignola et al., 1994). α-Conotoxins which bind to neuronal type nicotinic receptors are suitable for preventing the proliferation of tumors such as SCLC and can be used therapeutically to inhibit such proliferation as described below. These α-conotoxins can also be used diagnostically for detecting the presence and/or location of small-cell lung tumors as described below. Although Codignola et al. (1994) report that α-conotoxin MI binds to these SCLC receptors, α-conotoxin MI is not suitable for therapeutic or diagnostic use since it also binds to neuromuscular receptors and can cause paralysis which could lead to death. α-Conotoxins which do not bind to neuromuscular receptors or which have a much lower affinity for such receptors as compared to the nicotinic neuronal receptors are suitable for therapeutic or diagnostic purposes. Such peptides include the α-conotoxins MII and ImI.

Example 13

Diagnosis of SCLC Using α-Conotoxins

α-Conotoxins which bind to SCLC nicotinic receptors can be used for diagnosing SCLC tumors in patients. Suitable α-conotoxins include MII, ImI, PnIB and PnIA A10L. Administration of a labeled conotoxin to a patient will reveal the presence of SCLC cells if any are present. The α-conotoxin is labeled with a radioactive marker, preferably iodine, e.g., $^{131}$I or $^{125}$I. Labeling can be performed by standard techniques well known in the art. Alternatively, a Tyr residue can be added to the N-terminus and iodinated as described above. The labeled toxin is administered intravenously in a range of 5–50 nmoles, preferably about 25 nmoles. The label is then detected by standard techniques well known in the art. The labeled toxins will bind to SCLC cells and also may bind to autonomic ganglia. However, the locations of autonomic ganglia are known and can be distinguished from signals resulting from binding of the labeled toxin to SCLC cells.

Example 14

Therapeutic Use of α-Conotoxins to Treat SCLC Tumors

α-Conotoxins which bind to SCLC nicotinic receptors can be used therapeutically to treat patients with SCLC tumors. Suitable conotoxins are those which do not bind strongly to muscle receptors, e.g., MII, ImI, PnIB and PnIA A10L. Patients who have been diagnosed with SCLC can have a suitable conotoxin administered, preferably intravenously or intramuscularly. A dose of 200–2000 nanomoles, preferably about 500 nanomoles, is administered. The dosing schedule depends on the in vivo stability of the specific conotoxin used. In general conotoxins are relatively resistant to degradation and may last on the order of a few days. Therefore a typical dosing schedule may be anywhere from twice per day to once every few days, this being dependent on the biological lifetime of the specific conotoxin used.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

Bodansky et al. (1966). *Chem. Ind.* 38:1597–98.
Cartier, G. E. et al. (1996a). *J. Biol. Chem.* 271:7522–7528.
Cartier, G. E. et al. (1996b). *Soc. Neurosci. Abst.* 22:268.
Cattaneo, M. G. et al. (1993). *Cancer Res.* 53: 566–5568.
Chini, B. et al. (1992). *Proc. Natl. Acad Sci. USA* 89:1572–1576.
Clarke, P. B. S. and Reuben, M. (1996). *Br. J. Pharmacol.* 111:695–702.
Codignola, A. et al. (1994). *FEBS Lett.* 342:286–290.
Cruz, L. J. at al. (1976). *Verliger* 18:302–308.
Cruz, L. J. et al. (1987). Conus geographus toxins that discriminate between neuronal and muscle sodium channels. *J Biol. Chem.* 260:9280–9288.
El-Bizri, H. and Clarke, P. B. S. (1994). *Br. J. Pharmacol.* 111:406–413.
Grady, S. et al. (1992). *J. Neurochem.* 59:848–856.
Gray, R. et al. (1996). *J. Neurochem.* 59:848–856.
Haack, J. A. et al. (1990). Contryphan-T: a gamma-carboxyglutamate containing peptide with N-methyl-d-aspartate antagonist activity. *J. Biol. Chem.* 265:6025–6029.
Horiki, K. et al. (1978). *Chemistry Letters* 165–68.
Kahn, R. S. and Davis, K. L. (1995). New Developments in Dopamine and Schizophrenia. In *Psychopharmacology: The Fourth Generation ofProgress*, Bloom, F. E. and Kupfer, D. J. (eds), Raven Press, New York, pp 1193–1203.
Kaiser et al. (1970). *Anal. Biochem.* 34:595.
Kapoor (1970). *J. Pharm. Sci.* 59:1–27.
Kornreich, W. D. et al. (1986). U.S. Pat. No. 4,569,967.
Kulak, J. M. et al. (1997). α-Conotoxin MII blocks nicotine-stimulated dopamine release in rat striatal synaptosomes. *J. Neurosci.* 17:5263–5270.
Lapehak, P. A. et al. (1989). *J. Neurochem.* 52:483491.
Maneckjee, R. and Minna, J. D. (1990). *Proc. Natl. Acad Sci. USA* 87:3294–3298.
Martinez, J. S. et al. (1995). *Biochem.* 34:14519–14526.
McGehee, D. S. and Role, L. W. (1995). *Annu. Rev. Physiol.* 57:521–546.
Mena, E. E. et al. (1990). Contryphan-G: a novel peptide antagonist to the N-methyl-D-aspartic acid (NMDA) receptor. *Neurosci. Lett.* 118:241–244.
*Methoden der Organischen Chemie* (Houben-Weyl): Synthese von Peptiden, E. Wunsch (Ed.), Georg Thieme Verlag, Stuttgart, Ger. (1974).
Mongeau, R. et al. (1997). The serotonergic and noradrenergic systems of the hippocamnpus: their interactions ant the effects of antidepressant treatments. *Brain Res. Rev.* 23:145–195.
Mulle, C. et al. (1991). *J. Neurosci.* 11:2588–2597.
Nishiuchi, Y. et al. (1993). Synthesis of gamma-carboxyglutamic acid-containing peptides by the Boc strategy. *Int. J. Pept. Protein Res.* 42:533–538.
Olivera, B. M. et al. (1984). U.S. Pat. No. 4,447,356.
Olivera, B. M. et al. (1985). Peptide neurotoxins from fish-hunting cone snails. *Science* 230:1338–1343.
Papke, R. L. et al. (1994). Inhibition of nicotinic acetylcholine receptors by bis(2,2,6,6-tetramnethyl-4r-piperidinyl) sebacate (Tinuvin 770), an additive to medical plastics. *J. Pharmacol Exp. Ther.* 268:718–726.
Pontieri, F. E. et al. (1996). Effects of nicotine on the nucleus accumbens and similarity to those of addictive drugs. *Nature* 383:255–257.
Rapier, C. et al. (1988). *J. Neurochem.* 50:1123–1130.
*Remington's Pharmaceutical Sciences*, 18th Ed., Mack Publishing Co., Easton, Pa. (1990).
Rivier, J. E. et al. (1978). *Biopolymers* 17:1927–38.
Rivier, J. E. et al. (1987). Total synthesis and further characterization of the gamma-carboxyglutamnate-containing 'sleeper' peptide from Conusgeographus. *Biochem.* 26:8508–8512.
Roberts et al. (1983). *The Peptides* 5:342–429.
Rowell, P. P. and Winkler, D. L. (1984). *J. Neurochem.* 43:1593–1598.
Sacaan, A. I. et al. (1995). *J. Pharmacol Exp. Therapeutics* 274:224–230.
Sambrook, J. et al. (1979). *Molecular Cloning*: A Laboratory Manual, 2nd Ed., Cold Spring Harbor Laboratory, Cold Spring Harbor, N.Y.
Schatzberg, A. F. and Nemeroff, C. B (eds) (1995). "Section II: Classes of psychiatric drugs: animal and human pharmacology." In *Textbook of Pharmacology*, Meltzer, H. Y. (ed), American Psychiatric Press, Inc., Washington, D.C., pp. 141–438.
Schroder & Lubke (1965). *The Peptides* 1:72–75, Academic Press, NY.
Schuller, H. M. et al. (1990). *Life Sci.* 47:571–578.
Schultz, D. W. and Zigmond, R. E. (1989). *Neurosci. Lett.* 98:310–316.
Shon, K.-J. et al. (1994). *Biochemistry* 33:11420–11425.
Sine, S. M. and Claudio, T. (1991). *J. Biol. Chem.* 266:19369–19377.
Stewart and Young, *Solid-Phase Peptide Synthesis*, Freeman & Co., San Francisco, Calif. (1969).
Tarroni, P. et al. (1992). *FEBS Lett.* 312:66–70.
Vale et al. (1978). U.S. Pat. No. 4,105,603.
Vidal, C. and Changeux, J.-P. (1993). *Neuroscience* 56:23–32.
Wilkie, G. I. et al. (1993). *Biochem. Soc. Trans.* 21:429431.
Wonnacott, S. et al. (1995). "Presynaptic nicotinic autoreceptors and heteroreceptors in the CNS". In *Effects of Nicotine on Pharmacological Systems II*, P. B. S. Clarke et al. (eds.), Birkhäiuser Verlag, Basel, pp. 87–94.
Zhou L. M., et al. (1996a). Synthetic Analogues of Contryphan-G: NMDA Antagonists Acting Through a Novel Polyamine-Coupled Site. *J. Neurochem.* 66:620–628.
U.S. Pat. No. 3,972,859 (1976).
U.S. Pat. No. 3,842,067 (1974).
U.S. Pat. No. 3,862,925 (1975).
PCT Published Application WO 96/11698.

What is claimed is:

1. A substantially pure α-conotoxin peptide selected from the group consisting of:

Gly-Cys-Cys-Ser-Leu-Pro-Pro-Cys-Ala-Leu-Asn-Asn-Pro-Asp-Tyr-Cys (SEQ ID NO:10);

Gly-Cys-Cys-Ser-Leu-Pro-Pro-Cys-Ala-Ala-Ser-Asn-Pro-Asp-Tyr-Cys (SEQ ID NO:11);

Tyr-Gly-Cys-Cys-Ser-Asn-Pro-Val-Cys-His-Leu-Glu-His-Ser-Asn-Leu-Cys (SEQ ID NO:3); and Gly-Cys-Cys-Ser-Asn-Pro-Val-Cys-Phe-Ala-Thr-His-Ser-Asn-Leu-Cys (SEQ ID NO:4).

2. The α-conotoxin peptide of claim 1 having the formula Gly-Cys-Cys-Ser-Leu-Pro-Pro-Cys-Ala-Leu-Asn-Asn-Pro-Asp-Tyr-Cys (SEQ ID NO:10).

3. The α-conotoxin peptide of claim 1 having the formula Gly-Cys-Cys-Ser-Leu-Pro-Pro-Cys-Ala-Ala-Ser-Asn-Pro-Asp-Tyr-Cys (SEQ ID NO:11).

4. The α-conotoxin peptide of claim 1 having the formula Tyr-Gly-Cys-Cys-Ser-Asn-Pro-Val-Cys-His-Leu-Glu-His-Ser-Asn-Leu-Cys (SEQ ID NO:3).

5. The α-conotoxin peptide of claim 1 having the formula Gly-Cys-Cys-Ser-Asn-Pro-Val-Cys-Phe-Ala-Thr-His-Ser-Asn-Leu-Cys (SEQ ID NO:4).

6. The α-conotoxin peptide of claim 2 wherein at least one of the Pro residues is replaced with hydroxyproline.

7. The α-conotoxin peptide of claim 2 wherein a Tyr residue is incorporated on the N-terminus.

8. The α-conotoxin peptide of claim 7 wherein the Tyr residue is substituted with one or two iodines.

9. The α-conotoxin peptide of claim 3 wherein at least one of the Pro residues is replaced with hydroxyproline.

10. The α-conotoxin peptide of claim 3 wherein a Tyr residue is incorporated on the N-terminus.

11. The α-conotoxin peptide of claim 10 wherein the Tyr residue is substituted with one or two iodines.

12. The α-conotoxin peptide of claim 4 wherein the Pro residue is replaced with hydroxyproline.

13. The α-conotoxin peptide of claim 4 wherein the Tyr residue is substituted with one or two iodines.

14. The α-conotoxin peptide of claim 5 wherein the Pro residue is replaced with hydroxyproline.

15. The α-conotoxin peptide of claim 5 wherein a Tyr residue is incorporated on the N-terminus.

16. The α-conotoxin peptide of claim 15 wherein the Tyr residue is substituted with one or two iodines.

17. A substantially pure α-conotoxin peptide having the fornula Xaa-peptide, wherein Xaa is Tyr, mono-iodo-Tyr or di-iodo-Tyr and peptide is selected from the group consisting of (a) a peptide having the amino acid sequence set forth in SEQ ID NO:5, (b) a peptide having the amino acid sequence set forth in SEQ ID NO:7, (c) a peptide having the amino acid sequence set forth in SEQ ID NO:8, (d) a peptide having the amino acid sequence set forth in SEQ ID NO:9, (e) a peptide having the amino acid sequence set forth in SEQ ID NO:12 and (f) a peptide having the amino acid sequence set forth in SEQ ID NO:13.

18. The α-conotoxin peptide of claim 17 wherein at least one of the Pro residues in the peptide is replaced with hydroxyproline.

19. The α-conotoxin peptide of claim 17 wherein a Trp residue in the peptide is replaced with bromotryptophan.

* * * * *